US008185414B2

(12) United States Patent
Law et al.

(10) Patent No.: US 8,185,414 B2
(45) Date of Patent: May 22, 2012

(54) SYSTEM AND METHOD OF PROCESSING A HEALTH INSURANCE CLAIM

(75) Inventors: Sharon Dawn Law, Linden (ZA); Michele Read, Edenvale (ZA); Helen Mary Kruger, Morningside (ZA); Jennifer Anne Noble Luckhoff, Cape Town (ZA); Willemina Jacoba Du Plessis, Houghton Estate (ZA); Willem Jacobus Schoeman, Northcliff (ZA); Clint Wesley Odendaal, Morningside (ZA); Jacobus Johannes Olwagen, Centurion (ZA); Harriet Sam Hung, Akasia (ZA); Pieter Lodewickus Vermeulen, Centurion (ZA); Sanet Kock, Lynnwoodridge (ZA); Wendy Joy Hanan, Glenhazel (ZA)

(73) Assignee: Medikredit Integrated Healthcare Solutions (Proprietary) Limited, Johannesburg (ZA)

(*) Notice: Subject to any disclaimer, the term of this patent is extended or adjusted under 35 U.S.C. 154(b) by 372 days.

(21) Appl. No.: 11/903,390

(22) Filed: Sep. 21, 2007

(65) Prior Publication Data

US 2009/0083079 A1    Mar. 26, 2009

(51) Int. Cl.
*G06Q 40/00*  (2012.01)
*G06Q 10/00*  (2012.01)
*G06Q 50/00*  (2012.01)

(52) U.S. Cl. .................. 705/4; 705/2; 705/3; 705/7.11; 705/40

(58) Field of Classification Search ....................... 705/4
See application file for complete search history.

(56) References Cited

U.S. PATENT DOCUMENTS

| 5,119,470 | A  | * | 6/1992  | Highland et al. ............... 706/48 |
|-----------|----|---|---------|---------------------------------------|
| 5,412,758 | A  | * | 5/1995  | Srikanth et al. ................. 706/59 |
| 5,704,044 | A  | * | 12/1997 | Tarter et al. ...................... 705/4 |
| 6,021,202 | A  | * | 2/2000  | Anderson et al. ............... 705/54 |
| 6,208,973 | B1 | * | 3/2001  | Boyer et al. ...................... 705/2 |
| 7,174,302 | B2 | * | 2/2007  | Patricelli et al. ................. 705/4 |
| 7,333,939 | B1 | * | 2/2008  | Stender et al. .................... 705/4 |
| 7,370,018 | B2 | * | 5/2008  | Bryant et al. ..................... 705/4 |
| 7,386,526 | B1 | * | 6/2008  | Chappel .......................... 706/47 |
| 7,441,022 | B1 | * | 10/2008 | Schuba et al. ............... 709/223 |
| 7,505,463 | B2 | * | 3/2009  | Schuba et al. ............... 370/392 |
| 7,512,071 | B2 | * | 3/2009  | Goldschmidt et al. ........ 370/235 |
| 7,617,119 | B1 | * | 11/2009 | Neal et al. ....................... 705/10 |
| 2002/0120473 | A1 | * | 8/2002  | Wiggins ............................ 705/4 |
| 2002/0169955 | A1 | * | 11/2002 | Bryant et al. ................. 713/153 |
| 2002/0198831 | A1 | * | 12/2002 | Patricelli et al. ............... 705/40 |
| 2003/0083906 | A1 | * | 5/2003  | Howell et al. .................... 705/4 |

(Continued)

*Primary Examiner* — Leland Marcus
(74) *Attorney, Agent, or Firm* — Frommer Lawrence & Haug LLP; Ronald R Santucci

(57) ABSTRACT

A system and method of processing a health insurance claim are provided. According to the method, transaction data is received that has been transmitted from a third party computer via an open communication channel with the third party computer. The transaction data relates to a health insurance transaction and includes at least a unique identifier for a beneficiary of a health insurance plan to whom the health insurance transaction relates and details of a transaction that is being requested to be processed. The transaction is processed while the communication channel remains open to ascertain if the transaction is an allowable transaction. In response to the transaction submitted, a message is transmitted via the open communication channel to the third party computer wherein the message indicates that the transaction has been processed and that the transaction is an allowable transaction with or without patient collection or that the transaction is not an allowable transaction. The system and method allow for multiple rules to be created for unique sets of circumstances using multiple or singular inputs across multiple health insurance plans using a single system.

35 Claims, 3 Drawing Sheets

U.S. PATENT DOCUMENTS

| | | | |
|---|---|---|---|
| 2003/0149594 A1* | 8/2003 | Beazley et al. | 705/2 |
| 2004/0044772 A1* | 3/2004 | Harkin | 709/227 |
| 2004/0177139 A1* | 9/2004 | Schuba et al. | 709/223 |
| 2005/0276262 A1* | 12/2005 | Schuba et al. | 370/389 |
| 2005/0278431 A1* | 12/2005 | Goldschmidt et al. | 709/207 |
| 2006/0013136 A1* | 1/2006 | Goldschmidt et al. | 370/235 |
| 2006/0041487 A1* | 2/2006 | Santalo et al. | 705/30 |
| 2006/0047539 A1* | 3/2006 | Huang | 705/4 |
| 2006/0085231 A1* | 4/2006 | Brofman | 705/4 |
| 2006/0166642 A1* | 7/2006 | Puthenpura et al. | 455/406 |
| 2006/0166643 A1* | 7/2006 | Puthenpura et al. | 455/406 |
| 2007/0005402 A1* | 1/2007 | Kennedy et al. | 705/4 |
| 2007/0005403 A1* | 1/2007 | Kennedy et al. | 705/4 |
| 2007/0027718 A1* | 2/2007 | Amerantes et al. | 705/3 |
| 2007/0043594 A1* | 2/2007 | Lavergne | 705/2 |
| 2008/0077459 A1* | 3/2008 | Desai et al. | 705/7 |

* cited by examiner

SYSTEM AND METHOD OF PROCESSING A HEALTH INSURANCE CLAIM

BACKGROUND OF THE INVENTION

THIS invention relates to a system and method of processing a health insurance transaction.

The processing of health insurance transactions occurs where a beneficiary of a health insurance plan, which may be either a member of the plan or a dependant of the member, receives a medical service or a medical product and then:

the member requests the health insurance plan or third party administrator to pay a third party service or product provider directly or to reimburse the member who has paid for the medical product or medical service; or alternatively the third party service or product provider submits the transaction on behalf of the member to the health insurance plan or third party administrator to pay the third party service or product provider directly or to reimburse the member who has paid for the medical product or medical service.

The present systems used to process these transactions are slow and very labor intensive with the transaction being sent to a system operated by a health insurance plan, third party administrator or via a third party clearing house. The health insurance plan, third party administrator or the third party clearing house adjudicates the transaction and assesses if it is covered by the member's health insurance plan and also, in some cases, to see if the member has funds available to cover the costs of the transaction.

However, the current labor intensive processing takes a number of days or weeks. Errors in the transaction submitted cause further delays with the transaction being rejected often without clear explanation and returned to the sender unprocessed.

There is therefore a need for a system and method that will process transactions in real-time and in a paperless way thereby enabling holistic financial and clinical patient management.

The present invention seeks to address this.

SUMMARY

According to a first embodiment there is provided a method of processing a health insurance transaction, the method including:

receiving transaction data transmitted from a third party computer via an open communication channel with the third party computer, the transaction data relating to a health insurance transaction, the transaction data including at least a unique identifier for a beneficiary of a health insurance plan to whom the health insurance transaction relates and details of a transaction that is being requested to be processed;

processing the transaction while the communication channel remains open to ascertain if the transaction is an allowable transaction;

in response to the transaction being allowable, transmitting a message via the open communication channel to the third party computer wherein the message indicates that the transaction has been processed and that the transaction is an allowable transaction with or without patient collection or that the transaction is not an allowable transaction.

The transaction being requested may be the payment of an amount of funds to the member or on behalf of the member to a third party and wherein the transaction data includes details of the medical service or medical product for which payment is being requested.

The processing of the transaction may also include ascertaining if the transaction is an allowable transaction with or without patient collection includes using the details of the member's health insurance plan to ascertain if the medical service or medical product is covered in terms of the member's health insurance plan.

In one example, the method further includes:

defining a plurality of criteria;

creating a plurality of rules wherein at least some of the rules include at least one of the plurality of criteria; and applying at least one rule to the transaction request.

At least some of the rules may include a plurality of criteria that are applied sequentially to determine if the transaction match the criteria and if so whether the transaction is an allowable transaction with or without patient collection.

In addition, different rules may include at least some of the same criteria, and only after all of the criteria of a rule have been applied to the transaction is the next rule applied to the transaction in a predefined sequence.

At least one of the rules may include one or more sub rules and wherein these sub rules are applied in a configured order.

In one example, if the transaction is an allowable transaction:

while the communication channel is open, transmitting a message to a server of a financial administration system via a second communication channel to determine if the member has funds available to pay the amount of the transaction;

receiving a response from the server of the financial administration system via the second communication channel indicating whether the member has funds available either in full or in part or no funds available to pay the amount of the transaction; and wherein the message transmitted to the third party computer via the open communication channel includes information on whether or not the member has sufficient funds available to cover the amount of the transaction.

In this example, if the server of the financial administration system is unavailable or too slow to respond, the transaction request is processed against last data stored in a database.

The results of the transaction may be stored on a database associated with the third party computer and on a database associated with a central server.

The results of the transaction may also be stored on a database associated with a financial administration system.

According to a second embodiment there is provided a system for processing a health insurance transaction.

a data receiving module for receiving transaction data transmitted from a third party computer via an open communication channel, the transaction data relating to a health insurance transaction, the transaction data including at least a unique identifier for a beneficiary of a health insurance plan to whom the health insurance transaction relates and details of a transaction that is being requested to be processed;

a processor for processing the transaction while the communication channel remains open to ascertain if the transaction is an allowable transaction;

a data transmitting module that in response to the transaction being allowable, transmits a message via the open communication channel to the third party computer wherein the message indicates that the transaction has been processed and that the transaction is an allowable transaction with or without patient collection or that the transaction is not an allowable transaction.

The transaction being requested may be the payment of an amount of funds to the member or on behalf of the member to a third party and wherein the data receiving module receives transaction data including details of the medical service or medical product for which payment is being requested.

The processor may process the transaction to ascertain if the transaction is an allowable transaction with or without patient collection using the details of the member's health insurance plan to ascertain if the medical service or medical product is covered in terms of the member's health insurance plan.

In one example, the processor processes the transaction by:
defining a plurality of criteria;
creating a plurality of rules wherein some of the rules include at least one of the plurality of criteria; and
applying at least one rule to the transaction request.

At least some of the rules may include a plurality of criteria that are applied sequentially to determine if the transaction match the criteria and if so whether the transaction is an allowable transaction.

In addition, different rules may include at least some of the same criteria.

Only after all of the criteria of a rule have been applied to the transaction may the next rule be applied to the transaction in a predefined sequence.

In one example, at least one of the rules includes one or more sub rules and wherein these sub rules are applied in a configured order.

The system may further include:
the data transmitting module further, in response to the transaction being an allowable transaction, and while the communication channel is open, transmits a message to a server of a financial administration system via a second communication channel to determine if the member has funds available to pay the amount of the transaction;
the data receiving module receives a response from the server of the financial administration system via the second communication channel indicating whether the member has funds available either in full or in part or no funds available to pay the amount of the transaction; and
the data transmitting module further transmits via the open communication channel to the third party computer information including whether or not the member has sufficient funds available to cover the amount of the transaction.

If the server of the financial administration system is unavailable or too slow to respond, the processor may processes the transaction request against last data stored in a database.

DESCRIPTION OF PREFERRED EMBODIMENTS

Figure 1:
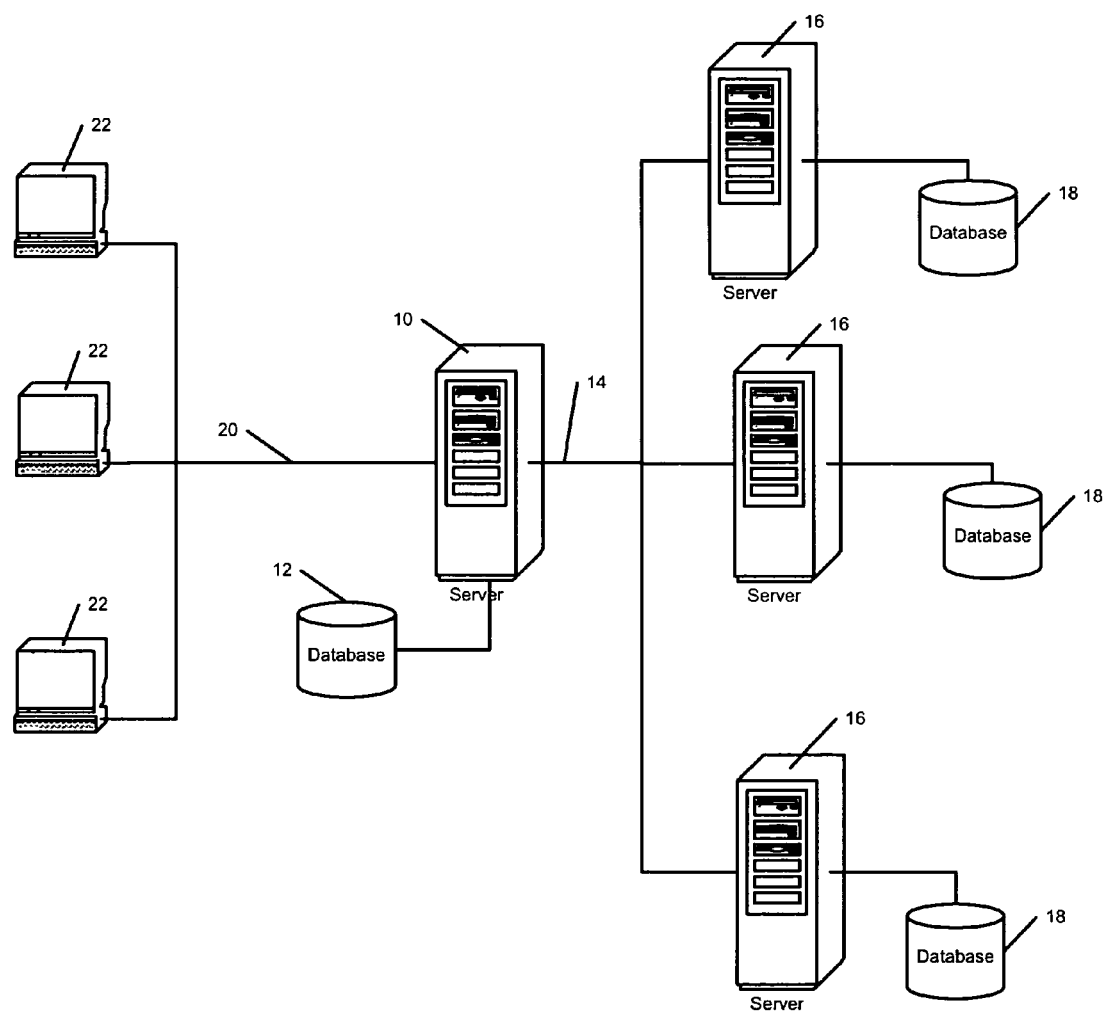
FIG. 1 shows an example system for processing a medical health insurance transaction.
Figure 2:
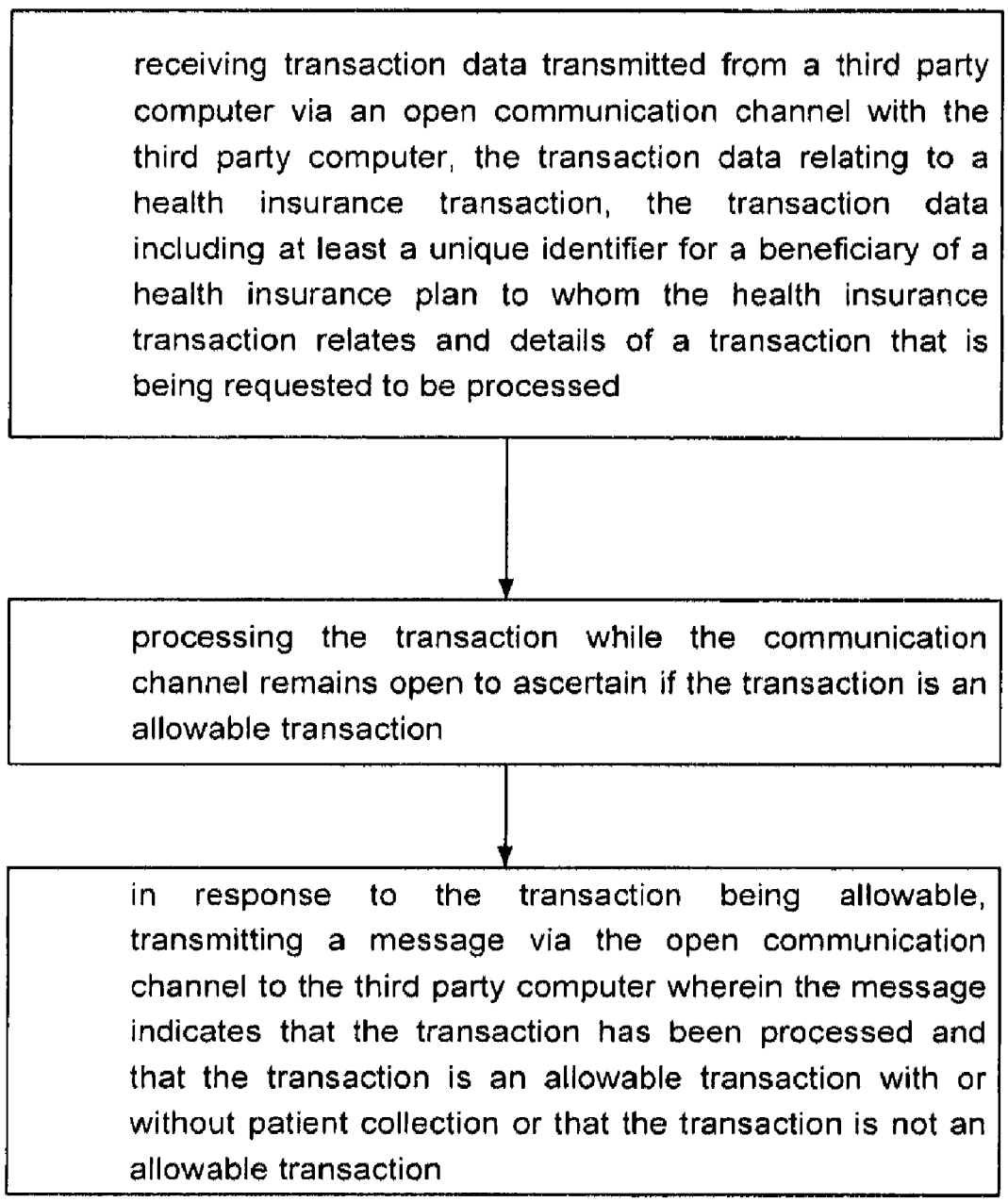
FIG. 2 shows an example method implemented by the system of FIG. 1.

Referring to FIG. 1, a system for processing a medical health insurance transaction includes a server 10 and an associated memory in the form of database 12.

The server 10 is connected by a first communications network 14 to a plurality of servers 16 of a financial administration system. These servers 16 could be servers of operators of different medical health insurance plans or third party administrators or financial institutions designated by health insurance plans, for example.

It will be appreciated that while only three servers 16 are shown there could be any number of servers.

Furthermore each of the servers 16 of the financial administration systems has at least one associated database 18.

The server 10 is also connected by a second communications network 20 to a plurality of third party computers 22.

The first and second communications networks may be the same or different communications networks.

It will be appreciated that while only three computers 22 are shown there could be any number of computers 22.

It will also be appreciated that the computers 22 could be any kind of computers including personal computers, laptop computers, servers, personal digital assistants and mobile telephones to name but a few examples.

In any event, each of the computers 22 represents a practice management system typically located at the rooms of a doctor, hospital, pharmacy or any other health care provider, for example.

Alternatively, at least some of the computers 22 could be the computers of members of a health insurance plan.

In any event, in order to maintain the speed and accuracy of the system, the architecture of the server 10 is a dual modular redundancy system which ensures continuous availability of the server 10.

The replicated components process the same instructions at the same time so that if a component malfunctions, the active spare continues with no system downtime and data loss.

It will be appreciated that the server 10 will typically include at least one processor that may include modules which are implemented by a machine-readable medium embodying instructions which, when executed by a machine, cause the machine to perform any of the methods herein.

It will be appreciated that embodiments of the present invention are not limited to such architecture, and could equally well find application in a distributed, or peer-to-peer, architecture system. Thus the modules could be located on one or more servers operated by one or more institutions.

In any event, the computers 22 are used to access the server 10 and to forward medical health insurance transactions to the server 10 as will be described in more detail below.

The server 10 then processes the health insurance transaction received.

This occurs as follows. Transaction data transmitted from a third party computer 22 is received at the server 10.

For purposes of embodiments of the present invention the following types of transactions can be distinguished for real-time processing handling:
Eligibility transactions;
Items (for example an individual medical product and/or medical service codes);
Claims (i.e. a single event with multiple items);
Cases: This transaction type is typically used by hospitals, clinics, etc. Case management is conducted by recognizing each individual item submitted as a separate transaction and grouping the individual transaction items together as a case which will be identifiable under a unique case number. Cases consist of:
A full case record detailing the individual line items for an entire episode ranging from the open case instruction to the close case instruction; or An interim case record which also contains an open case instruction and a closed case instruction for the interim period but the case is sent with an interim indicator; or Amendments being additional line items to a closed case which were not submitted with the original case record.

Reversals (i.e. cancellation of previous transaction in real time);

Once processed, the final status of the transaction could be:

Approved or processed item, claim or case with or without Risk Management Responses and co-payments/patient collection;

Rejections (at item, claim or case level) i.e. denial of benefit;

Duplicates: Duplicate transactions can be identified at item level or claim level or case level using specified criteria.

This system has the ability to process transactions at either item level or claim level or case level and the accompanying interventions and responses can then be sent as either item level, claim level or case level.

The item, claim or case transaction data relates to a health insurance transaction and includes at least an unique identifier for a beneficiary (member or dependant) of a health insurance plan to whom the health insurance transaction relates, an amount of funds being requested to be paid to the member or on behalf of the member and details of the medical service or medical product for which payment is being requested.

Eligibility transactions can be conducted in respect of the following:

Whether a patient is a valid beneficiary of a health insurance plan?

Whether a patient has funds available in respect of his/her health insurance plan option?

Whether funds are available for a specific medical product and/or service?

Whether there is a treatment protocol in place for the specific patient in respect of his/her specific disease condition?

The server 10 processes the transaction. In one example this includes ascertaining if the medical service or medical product for which payment is being requested is covered by the member's health insurance plan.

The initial validations performed on the transaction ensure basic data integrity including that the key components of the transaction are valid according to gate keeping rules, such as:

Population of mandatory fields;

Validation against industry files such as files listing valid, registered healthcare providers, active medical product codes, active medical service codes, for example;

The transaction is active and not stale;

Transaction source validation—the source is accredited to submit transactions;

Validation of the message structure of the transaction;

Various duplicate checking rules are applied over a pre-defined period;

Dynamic member plan management—allowing the sender of the transaction to utilize one option code and the system will determine through various hierarchies which plan the patient belongs to and access the various rule sources;

Validation against pre-defined lists on the system—such as allowed healthcare provider types and disciplines and allowed medical product and service codes, for example;

Whether or not the data supplied on an item describing the health product or service is within a clinically accepted parameter as loaded on database 12.

It will be appreciated that the above is not an exhaustive list of validation checks that may be undertaken.

In addition to the initial validations performed, adjudication rules are then applied. This is accomplished by the server 10 using a rules engine which operates on rule stacking, which offers complex rule applications in a scalable and flexible manner on all transaction types i.e. a heuristic computerized framework to dynamically create situation specific rules. The requirements of the system demand complexity in the data manipulated, as well as complexity in the rules processed against the data. A single claim may have several hundred items associated with it, and each claim can contain in excess of 120 distinct pieces of information to be processed.

Figure 3:
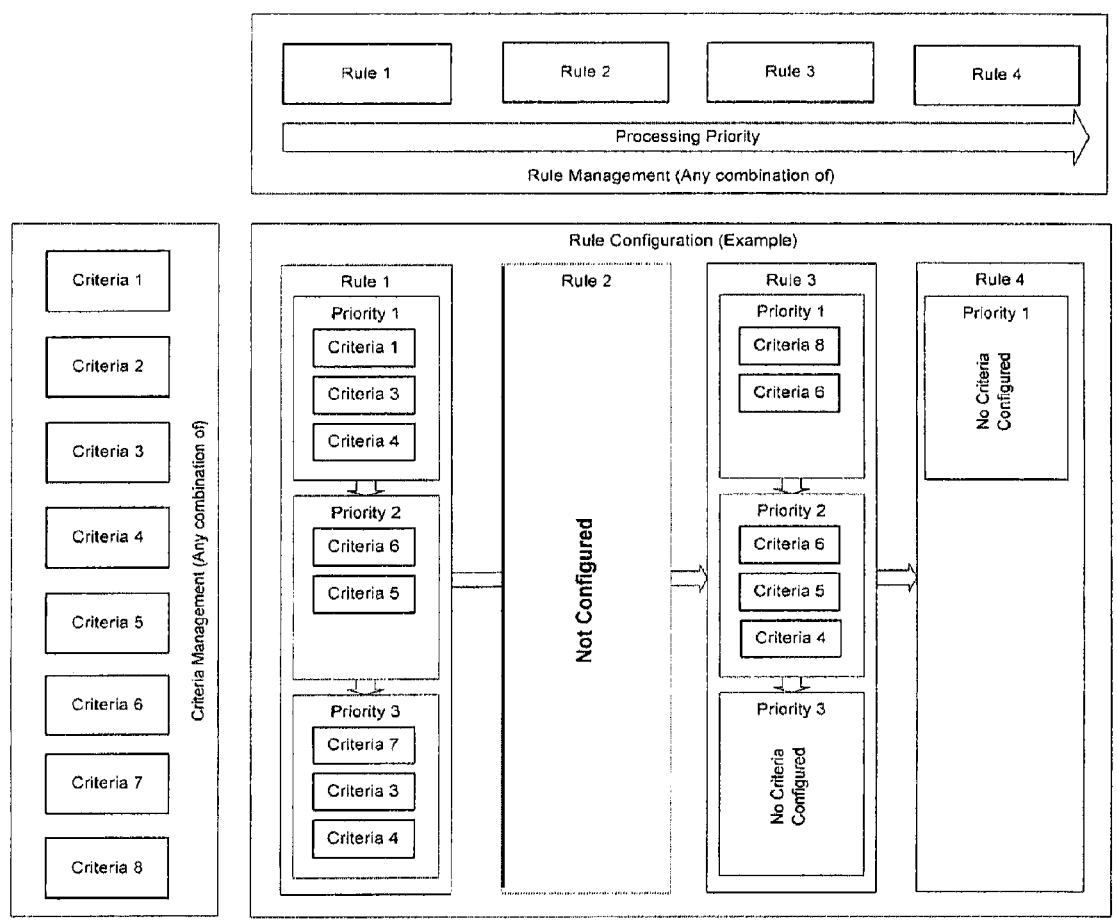
FIG. 3 shows an example of how rules are created based on criteria and combined to define the processing rules for a health insurance plan on server 10 referred to in FIG. 1.

Referring to FIG. 3, the rules database is designed to allow unlimited health insurance plan rules to be configured on the system, with an infrequent requirement for customization. This is achieved by utilizing a combination of criteria with rules types. A hierarchy for these rules is then determined and applied in real time.

The rules database has a predefined list of criteria, which when selected as a single criterion, or in combination with other criteria, defines the specific circumstance in which a rule must be applied. This is referred to as criteria stacking to define a rule.

Thus, a plurality of criteria are defined and thereafter a plurality of rules are created wherein each rule includes at least one of the plurality of criteria and wherein different rules include at least some of the same criteria.

Typically each of the rules includes a plurality of criteria that are applied sequentially to determine if the transaction is an allowable transaction and only after all of the criteria of a rule have been applied to the transaction is the next rule applied to the transaction.

Examples of criteria could be healthcare provider types;

discipline types;

networks (for example financial and/or clinical rules can be applied to enforce any arrangement between a health insurance plan and its designated network, or patient rules can override network arrangements, or in instances where a healthcare provider belongs to more than one network, priority can also be defined in respect of these networks for each rule type, etc.);

nature of medical products;

nature of medical service codes;

protocols (for example a health insurance plan can set protocols and limits for a disease condition for specific disciplines);

patient demographics (for example age and gender appropriateness);

geographical area;

health insurance plan identifier;

selected list of health products or services, network of healthcare providers;

preauthorized health product or medical services for a specific patient;

benefit type (for example insured benefit or savings account benefit).

Examples of rule types could be: member co-payment/patient collection as a percentage/sliding scale or fixed amount of the approved calculated amount; health product or service exclusion; health product or service pricing rule, including discounts, mark-ups; quantity limits, etc If the same rule must be applied in a different way dependent on the criteria defined, the priority or sequence in which the rules must be applied, is predefined in the rules database for the health insurance plan. The default rule will have the lowest priority. This is referred to as rule stacking. An example of this could be: Rule 1 priority 1—apply a 20% patient co-payment if the patient receives health services from network A, Rule 1, priority 2—apply a 30% co-payment/patient collection on approved amount if patient receives the health service from network B, Rule 1, priority 3: between $0-99.99 apply 35% patient co-payment/patient collection and between $100-infinity apply 35% capped at $50 if patient receives health services from any other healthcare provider registered to submit claims. This third rule is the default rule and only applies if the data supplied on the claim does not match priority 1 or 2 rule.

In addition, different rule types are applied in a predefined sequence in order to ensure that the logical calculation and processing of the item on the claim occurs.

Multiple rules can therefore be created for unique sets of circumstances using multiple or singular inputs, such as:
  blacklisting (for example a health insurance plan can elect to set-up a black list which consists of suppliers which are not allowed to supply medical products and/or medical services to their beneficiaries;
  capitation rules (for example the capitation agreement can span multiple provider types and multiple groups, value and/or quantity limits can be set at element level or multiple levels, and/or benefits can be identified that will be costed outside the capitation arrangement, etc.);
  appropriate level of care rules;
  clinical appropriateness rules (for example quantity limits for medical products and/or services, excessive quantity for medical products and/or services, days of therapy limits, duplicate checking for medical products and/or services, overcoding, etc);
  interval rules (for example the application of fixed or rolling benefit periods, or a quantity can be defined specific to a patient for a specified time period, or medical services can be limited per period, etc.);
  financial rules (for example reference pricing, or the application of pricing methodology to enable compliance with legislation, etc. Pricing rules can be configured at a health insurance plan option level or health insurance plan option/network level or rule stacking level, etc. Pricing rules can also be set at fixed values, tiered values, % values, sliding scales, etc.);
  rules for a particular health insurance plan option;
  benefit type rules (for example multiple benefit types submitted on the same transaction can be processed on individual benefit type rules);
  patient specific rules;
  exclusion rules (for example exclusion sets can be created for a health insurance plan);
  stale transaction periods and/or resubmission stale transaction periods as set by applicable regulatory frameworks or health insurance plans;
  specific rules to enforce certain applicable regulatory requirements.

In addition, as illustrated in FIG. 3, any rule can include one or more sub rules referred to as "priority" in the drawings. Each of these includes a plurality of criteria. The sub rules are applied in the order of their priority.

Where the lowest priority sub rule is configured for a particular rule, this will be the default application for that particular rule.

It must be appreciated that there is neither a limitation on the number of multiple rules that can be created nor a limitation on the number of multiple or singular inputs that can be used in the creation of such rules.

All rules are effective and termination date driven which allow for future dated rules, limited period patient rules, indefinite period rules, etc.

A very simplistic practical example of where rule and criteria can be combined in a predefined hierarchy is set out below:
  If patient is a male and over the age of 18, medical product A if obtained from certain provider discipline types will be allowed for a specific health insurance plan option X up to an amount of Y provided that funds are available. This rule can be further configured to apply quantity and interval management that the transaction will only be allowed if 30 tablets are used over a period of 1 month for 6 consecutive months;
  An exception to rule 1 is created whereby if the patient is a female and over the age of 18, medical product A if obtained from a specific provider discipline type will be allowed for a specific health insurance plan option X up to an amount of Z provided that funds are available. This rule can be further configured to apply quantity and interval management that the transaction will only be allowed if 30 tablets are dispensed once off during a calendar year;
  If the patient is a female, under the age of 18 and has obtained the necessary authorization for a specified quantity of medical product A for a specified period, medical product A if obtained from certain provider discipline types will be allowed for a specific health insurance plan option X with no financial benefit limit being applied;
  As result of a history of abuse of medical product A, a specific patient as identified by an unique patient identifier will be excluded under all circumstances from obtaining medical product A from any provider discipline type for a specific health insurance plan option X for a period of a calendar year;
  If none of the above rules apply, health insurance plan option X will not allow any transactions for medical product A.

Apart from it being possible to create multiple rules for unique sets of circumstances using multiple or singular inputs, different tailored data rich risk management responses can be created for each such unique set of circumstances. For example, in one instance when applying the same set of rules, a health insurance plan may elect to reject a transaction, whereas in another instance, applying the same set of rules, another health insurance plan may elect to rather partially pay for the transaction resulting in patient collection.

In addition to determining whether the medical service or medical product is covered by the member's health insurance plan, a number of other issues are also taken into account to determine whether the transaction is allowable.

For example, a rule will be created where the patient history data is accessed and the patient's history including previous services and medical products used by the member are taken into account. This would include diagnostic procedures, services from various healthcare providers such as specialists, physicians, nurses and other healthcare professionals as well as any medication that the patient has received.

Example of the above
  Rule 1: The transaction for a medical service received by the patient will be processed and approved if the service is not the same than a service received from a similar healthcare provider in a pre-determined time period.

Rule 2: If the service is received from a similar or equivalent provider for the same condition the transaction will be processed but the patient must pay for the service and not the healthcare insurance plan.

Rule 3: If the transaction is for a medial product that is not related to the medical service for which a transaction was processed and is contained in the patient history, the transaction would not be payable by the healthcare insurance plan.

Rule 4: If the transaction is for a medical product that is related to the service for which a transaction was processed and which information is contained in the patient history file the transaction will be a valid claim and will be paid by the healthcare insurance plan.

The server uses a number of data files stored in the associated database 12 which are accessed by the server to make the decision as to whether the transaction is allowable or not. For example, the database will store a member file, a health insurance plan file, a healthcare provider file, a product file, a service file and a clinical master file which are all accessed to process and adjudicate the transaction. The member file includes unique beneficiary identifiers, benefit effective and termination dates, status of the beneficiaries' membership, financial balance per benefit type as at the run date and time, and any patient specific preauthorisation/exclusions for a specific health product/service or protocol and patient specific rule instructions.

In addition to current regulatory frameworks which define medical treatment service codes, industry guides exist which define under which circumstances these services can be performed and by whom. To apply industry guides in an on line real time environment, there is a need to translate these industry guides into a rules engine and the system has this capability. The server contains a rules engine which enables a business user to load the guidelines as rules which are applicable during the system adjudicating and processing of a transaction. Rules can further be configured for specific requirements of health insurers. For example, there are specified procedures which can only be performed on a specific age group by a specific provider/discipline type or another example where a follow-up consultation cannot take place unless there was a previous consultation performed.

The clinical rules applied to each healthcare transaction are multidimensional as they relate to clinical appropriateness of the treatment based on established clinical practice and the unique requirements of the patient in question.

Clinical rules are linked to financial rules, inter alia, through clinical sets developed for specific diseases. The linking of the sets with financial rules allows highly flexible pricing methodologies. For example a service for a specific disease type can be priced at a certain amount X if the service is obtained from any one of a group of healthcare providers that form a healthcare provider network. In the event that the service is obtained from a healthcare provider not belonging to the network in question, the services may be priced at amount Y resulting in patient collection. The clinical rules used during the transaction processing take into account the appropriate treatment guidelines for the disease diagnosed, the inter relationship between the diagnosis, services, medicines and other medical products and in addition, interval and quantity management in respect thereof. This information is also used to determine if the transaction is an allowable transaction or not.

Financial rule management assists the health insurance plan, the healthcare provider and the patient. The financial rules take into account the financial rules of the health insurance plan which could be based on contractual arrangements between the health insurance plan and the provider as well as ensuring compliance to regulatory frameworks such as financial rounding rules, regulated price lists, tax calculations. Pricing rules can thus be set as for example, a fixed fee, % mark-up, tiered or sliding scales.

Enforcing the contractual arrangements between the health insurance plan and the healthcare provider may result in an overcharge which is sent back as due by the healthcare provider and not due by the patient.

Financial rule management also allows for the healthcare provider to have specific pricing and a sophisticated pricing hierarchy. For example, a network of healthcare providers may contract with a health insurance plan to render services to its beneficiaries at a certain preferential pricing structure.

The financial rule management also caters for patient collection enforcing the health insurance plan option rules for which the patient has registered such as:

Defined fixed levies applicable for specific transaction types;

Variable collection rules based on the results of the rule stacking application;

Healthcare Provider/Network based collection—e.g. if the patient goes outside the designated network the patient is liable for a co-payment;

Beneficiary status self-payment portion—based on the patient's current standing with the health insurance plan, a self payment portion will be determined.

Interval management such as early re-fill of medical product and medical service quantity management can also be configured with defined risk management responses to ensure that the patient is liable for the excess portion. (Note this can also be configured as a rejection of the transaction.)

An example of variable collection rules would be unit reference pricing (a pricing methodology for a single healthcare event) and limits reference pricing (a pricing methodology for a series of healthcare events over a defined period of time e.g. a condition limit value which will accumulate the costs of medical products and services and defines what the health insurance plan is prepared to reimburse the provider and the excess is due by the patient.).

Another example of financial rule application would be where the healthcare insurance plan uses sophisticated over-coding methodologies to determine the amount that will be paid:

Rule 1: A patient with disease condition X will have access to certain medical products and services based on the insurance plan option of their choice. The transaction is for a medical product/service that is not specifically listed in the plan option. The over-coding system will be accessed to determine if the transaction is valid for the treatment of disease condition X despite the fact that the insurance plan does not specifically cover the medical product/service. If the transaction is a valid transaction in terms of the clinical appropriateness rules, the transaction will be approved with the resulting financial patient pay response message returned to third party computer 22.

Rule 2: If the transaction is for a medical product/service not specifically listed in the plan and the treatment is in terms of the over-coding system clinically inappropriate for the treatment of disease condition X, the transaction will not be approved and a clinical and financial message will be returned to the third party computer 22.

It should also be noted that the system has the ability to process a healthcare transaction in full if all the clinical and financial rules are provided and that no further processing is required. If all healthcare transactions are processed through this system, no further duplicate checking would be required.

The server 10 processes the transaction request in real-time and the server 10 is specifically developed for speed and accuracy and to process high volumes of transactions concurrently. This is accomplished by an application architecture which is designed for performance and scalability supporting the real time requirement of speed and accuracy. The application design is multi-threaded for concurrent processing. In a test of a prototype server 10, it was found that the complete processing time was between 0.2 and 0.6 seconds excluding the communication time between the various components namely computer 22, communication network 20, communication network 14, the server of a financial administration system 16 and database 18.

True real time processing is achieved by means of synchronous communication between the server 10 and the computers 22 and the servers 16.

Asynchronous communication occurs where a communication connection is opened between two parties to send the transaction request and then closed thereafter. To send a response to the request, a new communication connection is opened and then closed thereafter.

In contrast, with the present invention, the communication connection is opened to send the transaction request and then while the connection is still open, the response to the request is sent via the same connection before the connection is closed. Thus the communication channel between the server 10 and the computers 22 and the servers 16 is kept open while the transaction is being processed.

During the transaction processing, messages will be returned to the sender of the transaction in real-time should the information in the transaction be incorrect or not allowed in terms of the clinical or financial rules applied to the transaction. This allows the sender to correct the information and resend the transaction immediately.

It should be appreciated that this is not a reversal of a transaction but is a partial process which allows the transaction to be revised, adjusted or corrected and resent.

If the transaction is determined to be allowable, a message is transmitted to a server of a financial administration system 16 to determine if the member has funds available to pay the amount of the transaction. This also occurs in real-time. If server of a financial administration system 16 is unavailable for whatever reason or too slow to respond, server 10 can process the transaction request against the last rules loaded on server 10. This is called "stand-in processing" and is an optional service. Stand-in processing will include a check as to whether or not the beneficiary has sufficient funds available for the health service/product item requested in their relevant benefit pool of their healthcare insurance plan. This information is obtained from the beneficiary file received either via daily batch or single record upload from the healthcare insurance plan.

The server of a financial administration system 16 is typically a server operated by a health insurance plan or third party administrator or banking institution designated by a health insurance plan The server of a financial administration system 16 will determine if the funds are available and if so will transmit a message back to the server 10 indicating either that the funds are available or that the funds are not available or that insufficient funds are available that may result in patient collection. This will result in instant benefit booking/deduction on server of a financial administration system 16.

It will be appreciated that because the transaction processing is occurring in real-time, the server of a financial administration system 16 could be configured to immediately include the amount into the payment run scheduled to pay the medical service provider or refund the member, as required.

The server 10 thus receives a response from the server of a financial administration system 16 indicating whether the member has funds available or not to pay the amount of the transaction.

The server 10 in turn transmits a message to the originating third party computer 22.

It will be appreciated that the message transmitted back to the originating third party computer 22 will indicate that the transaction is successfully processed if the transaction is an allowable transaction and if the member has funds available to pay the amount of the transaction. The message will indicate that the transaction has not been successfully processed if either the transaction is not an allowable transaction or if the member does not have funds available to cover the amount of the transaction.

The messages returned after processing can be customized in accordance with the requirements of different health insurance plans. In order to accomplish this, the customized messages are contained in a file stored in database 12. These customized messages are accessed and transmitted to the third party computer 22, as required.

Because the system is an intelligent system that uses a comprehensive set of rules to perform the transaction processing, and because the messages returned are information rich, the transaction responses can be used for discussion purposes with the patient at the point of service.

In testing of the prototype of the present invention, it was found that the full process from sending a transaction request to receiving a returned message, while dependent on the communications infrastructure used and the response time from server 16, ranged from between a few seconds to 20 seconds.

Once the transaction is received back at the third party computer 22, if the third party computer 22 is a practice management system, the results of the transaction can be written back into the member's financial and patient information file of the practice management system so that there is only one final version of the transaction.

It will also be appreciated that because the transaction is processed in real time, the sender of the transaction can, based on the information of a fully system processed and adjudicated transaction, inform the patient at the point of service while the patient is still with the healthcare provider of the following:

Of any clinical risk management response such as clinical appropriateness (for example the medical product/service requested is not appropriate for the condition of the patient based on the available patient history);
  Of any patient collection portion due as well as the associated risk management response i.e. the reason for the collection for example Limits Reference Pricing.

The patient is then empowered with the assistance of the healthcare provider to change the treatment accordingly. For example, the medical product can be substituted with another product.

This greatly assists the sender with financial risk management as well as assisting both the patient and the healthcare provider in making decisions regarding affordable and clinically appropriate treatment within the healthcare insurer's protocols and rules.

In addition, the sender of the transaction is provided with the ability to reverse the transaction in real-time if:

the patient decides that he/she would like to switch to a cheaper or different product or if he/she has subsequently negotiated with the sender a different pricing structure for the services delivered; or the healthcare provider decides to correct or amend his/her transaction based on information returned on the transaction response This is accomplished by the sender using the third-party computer 22 to transmit a reverse transaction request to the server 10.

The reverse transaction request will include at least an identification of the transaction.

This will be received by the server 10 that will in response send an instruction to the relevant server 16 to reverse the transaction.

In response, the server 16 will process and reverse the transaction and send a confirmation that the transaction has been reversed to the server 10 that will in turn send a response back to the third party computer 22.

Once the reversal confirmation is received back at the third party computer 22, if the third party computer 22 is a practice management system, the results of the transaction can be written back into the member's financial and patient information file of the practice management system so that there is only one final version of the transaction.

Obviously, the sender can now compile and send a new transaction for processing.

It will be appreciated that the clinical and financial master files stored in the database 12 need to be uploaded and updated regularly. This could be done using bulk uploads, typically at off peak hours, or by means of trickle feed directly into the rules engine. Clinical and financial rules can be loaded or amended at insurance plan level or unique patient level directly on database 12 or via trickle feed. These clinical and financial rules can be activated with immediate effect or a future effective date.

It will also be appreciated that in a large rollout of the system, there will be a very large number of third-party computers 22 accessing the server 10. These third-party computers 22 will typically be run by different practice management software.

In order to facilitate communication between the software operating on the third-party computers 22 and the server 10, a communication interface module (not shown) is loaded onto the third party computers 22.

This communication interface module is typically a software application that is agnostic and can interface with the various practice management applications using any available operating system such as DOS, Linux, Unix or Windows, to name but a few examples.

It is the communication interface module that acts as the interface between the server 10 and the practice management software operating on the third-party computers 22. Thus the communication interface module receives transaction data from the practice management software, packages this into the correct format and transmits this to the server 10.

The server 10 defines the correct format for the practice management software based on predefined indicators on the incoming transaction. On receipt of a response from the server 10, the communication interface module decrypts the response back into the correct format for the practice management software as predetermined by server 10.

The communication interface module includes a detailed transaction and technical log which is used to provide a full audit trail of each transaction sent and responded to in respect of computers 22. Each transaction is date and time stamped and has a unique reference number that is generated by the server 10. It will be appreciated that this makes the process fully auditable as well as traceable and all transactions can be accounted for. Furthermore, a single transaction can be tracked throughout all the systems as per FIG. 1.

The practice management system is accredited to electronically update the response received from server 10 into the database of computer 22. This negates the requirement for the user to manually capture the response and prevents data capture errors. In addition, as part of the accreditation/certification requirements, when writing back the response into the practice management system database, a clear separation is made between patient portion and health insurance plan portion. Computer 22, server 16 and server 10 then immediately have identical information relating to the risk management responses and the financial information relating to the healthcare transaction returned at the point of service.

In addition, the communication interface module does a basic validation that all mandatory fields have been included before a transaction is transmitted to the server 10.

The communication interface module also encrypts and decrypts data for transmission and receipt over the communications network 20.

It will be appreciated that the communications network 20 is preferably, but not necessarily, a secure network, for example a point-to-point digital connection, X.25, X.29 or a secure managed virtual private network across the Internet. In any event, the system is based on standards for data interchange, while still being flexible in the integration with the diverse range of communication networks, server 16 and computers 22. Full integration testing of all components is undertaken before production interconnection.

The entire system architecture is based on security standards to ensure the security and confidentiality of transactions, and utilizes encryption and cyclic redundancy checking to prevent unauthorized interception and interference with transactions.

We claim:

1. A method of adjudicating a health insurance transaction, the method including:

receiving transaction data transmitted from a third party computer via an open communication channel with the third party computer, the transaction data relating to a health insurance transaction, the transaction data including at least a unique identifier for a beneficiary of a health insurance plan to whom the health insurance transaction relates and details of a transaction that is being requested to be adjudicated;

executing instructions by a computer processor to adjudicate the transaction while the communication channel remains open by applying rules to fully adjudicate the transaction; and responding while the communication channel remains open whether the transaction will be paid or will not be paid or will be partially paid.

2. A method according to claim 1 wherein the transaction being requested is the payment of an amount of funds to the beneficiary or on behalf of the beneficiary to a third party and wherein the transaction data includes details of the medical service or medical product for which payment is being requested.

3. A method according to claim 2 wherein the adjudication of the transaction includes using the details of the beneficiary's health insurance plan to ascertain if the medical service or medical product is covered in terms of the beneficiary's health insurance plan.

4. A method according to claim 1 further including:
creating a plurality of rules, at least some of the rules including one or more sub-rules, wherein at least some of the sub-rules include selected ones of a plurality of criteria and some different ones of the plurality of criteria, wherein the sub-rules in a particular rule are applied in sequence of priority to determine whether the transaction data matches the criteria in a sub-rule of the particular rule;
wherein the criteria are selected from a list of criteria defined before receiving the transaction data,
selecting at least one of the plurality of rules, the received transaction data matching every criteria in a sub-rule of the selected rule;
determining a highest priority sub-rule of the selected rule having every criteria matching the transaction data; and
applying the highest priority sub-rule of the selected rule to the transaction request.

5. A method according to claim 4 wherein selected rules are applied sequentially to the transaction to determine whether the transaction is an allowable transaction and, when the transaction is allowable, then determining an amount due from the beneficiary based on the applied rules.

6. A method according to claim 5 wherein only after all of the criteria of a rule have been applied to the transaction is the next rule applied to the transaction in a configured sequence.

7. The method according to claim 5, wherein a default sub-rule is a sub-rule having the lowest priority of a particular selected rule such that the default sub-rule is applied when the transaction data does not match the criteria of any higher priority sub-rule of the particular selected rule.

8. The method of claim 7, further comprising applying a default rule to the transaction sequentially after all the selected rules have been applied.

9. The method according to claim 5, wherein a rule is not applied when the transaction data does not match all of the criteria of any sub-rule of a particular selected rule.

10. A method according to claim 4 wherein at least one of the rules includes one or more sub rules and wherein these sub rules are applied in a configured sequence.

11. A method according to claim 1 further including ascertaining whether the transaction for which payment is requested is covered by the health insurance plan of the beneficiary and determining whether benefit values are available for the beneficiary.

12. A method according to claim 11 wherein the ascertaining whether the transaction for which payment is requested is covered by the health insurance plan of the beneficiary and determining whether benefit values are available for the beneficiary includes communicating with a server of a financial administration system and includes:
transmitting, while the communication channel remains open, a message to the server of a financial administration system via a second communications channel; and
receiving, via the second communications channel, a message from the financial administration system server while the communication channel remains open that there are benefit values available or there are no benefit values or that only a portion of the benefit values are available for the beneficiary.

13. A method according to claim 11, wherein the checking to see whether the beneficiary has funds available to pay the claim includes checking data stored in a database.

14. A method according to claim 1 wherein the results of the adjudication are stored on a database associated with the third party computer and on a database associated with a central server.

15. A method according to claim 14 wherein the results of the adjudication are stored on a database associated with a payer system.

16. A system for adjudicating a health insurance transaction, the system including:
a data receiving module for receiving transaction data transmitted from a third party computer via an open communication channel, the transaction data relating to a health insurance transaction, the transaction data including at least a unique identifier for a beneficiary of a health insurance plan to whom the health insurance transaction relates and details of a transaction that is being requested to be adjudicated;
a processor for processing the transaction while the communication channel remains open by applying rules to fully adjudicate the transaction;
responding while the communication channel remains open whether the transaction will be paid or will not be paid or will be partially paid.

17. A System according to claim 16 wherein this transaction being requested is the payment of an amount of funds to the beneficiary or on behalf of the beneficiary to a third party and wherein the data receiving module receives transaction data including details of the medical service or medical product for which payment is being requested.

18. A system according to claim 17 wherein the processor processes the transaction using the details of the beneficiary's health insurance plan to ascertain whether the medical service or medical product is covered in terms of the beneficiary's health insurance plan.

19. A system according to claim 16 wherein the processor processes the transaction by:
creating a plurality of rules, at least some of the rules including one or more sub-rules, wherein at least some of the sub-rules include selected ones of a plurality of criteria and some different ones of the plurality of criteria, wherein the sub-rules in a particular rule are applied in sequence of priority to determine whether the transaction data matches the criteria in a sub-rule of the particular rule;
wherein the criteria are selected from a list of criteria defined before receiving the transaction data,
selecting at least one of the plurality of rules, the received transaction data matching every criteria in a sub-rule of the selected rule;
determining a highest priority sub-rule of the selected rule having every criteria matching the transaction data; and
applying the highest priority sub-rule of the selected rule to the transaction request.

20. A system according to claim 19 wherein selected rules are applied sequentially to the transaction to determine whether the transaction is an allowable transaction and, when the transaction is allowable, then determining an amount due from the beneficiary based on the applied rules.

21. A system according to claim 20 wherein only after all of the criteria of a rule have been applied to the transaction is the next rule applied to the transaction in a configured sequence.

22. A system according to claim 19 wherein at least one of the rules includes one or more sub rules and wherein these sub rules are applied in a configured order.

23. A system according to claim 16 wherein the data transmitting module further, while the communication channel is open, transmits a message to a server of a financial administration system via a second communication channel to ascertain whether the transaction for which payment is requested is covered by the health insurance plan of the beneficiary and determine whether benefit values are available for the beneficiary; and the data receiving module receives, via the second communication channel, a response from the server of the financial administration system while the communication channel remains open that there are benefit values available or there are no benefit values or that only a portion of the benefit values are available for the beneficiary.

24. A system according to claim 23, wherein the processor further checks to see whether the beneficiary has funds available by checking data stored in a database associated with the processor.

25. A system according to claim 16 wherein the results of the adjudication are stored on a database associated with the processor.

26. A system according to claim 16, wherein the processor further ascertains whether the transaction for which payment is requested is covered by the health insurance plan of the beneficiary and determines whether benefit values are available for the beneficiary.

27. A method of adjudicating a transaction, the method including:

receiving transaction data transmitted from a third party computer via an open communication channel with the third party computer, the transaction data including at least a unique identifier for a beneficiary of the transaction;

executing instructions by a computer processor to adjudicate the transaction while the communication channel remains open by applying rules to fully adjudicate the transaction; and responding while the communication channel remains open whether the transaction will be paid or will not be paid or will be partially paid.

28. A method according to claim 27, further including:

creating a plurality of rules, at least some of the rules including one or more sub-rules, wherein at least some of the sub-rules include selected ones of a plurality of criteria and some different ones of the plurality of criteria, wherein the sub-rules in a particular rule are applied in sequence of priority to determine whether the transaction data matches the criteria in a sub-rule of the particular rule;

wherein the criteria are selected from a list of criteria defined before receiving the transaction data, selecting at least one of the plurality of rules, the received transaction data matching every criteria in a sub-rule of the selected rule;

determining a highest priority sub-rule of the selected rule having every criteria matching the transaction data; and applying the highest priority sub-rule of the selected rule to the transaction request.

29. A method according to claim 28, wherein selected rules are applied sequentially to the transaction to determine whether the transaction is an allowable transaction.

30. A method according to claim 29, wherein only after all of the criteria of a selected rule have been applied to the transaction is a next rule applied to the transaction in a configured sequence.

31. The method according to claim 30, wherein a default sub-rule is a sub-rule having the lowest priority of a particular selected rule such that the default sub-rule is applied when the transaction data does not match the criteria of any higher priority sub-rule of the particular selected rule.

32. The method of claim 31, further comprising applying a default rule to the transaction sequentially after all the selected rules have been applied.

33. The method according to claim 30, wherein a rule is not applied when the transaction data does not match all of the criteria of any sub-rule of a particular selected rule.

34. A method according to claim 27, further including checking to see whether the beneficiary has funds available to pay for the transaction.

35. A method according to claim 34 wherein the checking to see whether the beneficiary has funds available includes communicating with a server of a financial administration system and includes:

transmitting, while the communication channel remains open, a message to the server of a financial administration system via a second communications channel to determine whether benefit values are available for the beneficiary; and receiving, via the second communications channel, a message from the server of a financial administration system while the communication channel remains open that there are benefit values available or there are no benefit values or that only a portion of the benefit values are available for the beneficiary.

* * * * *